US00PP30733P2

(12) United States Plant Patent
Hamilton et al.

(10) Patent No.: US PP30,733 P2
(45) Date of Patent: Jul. 23, 2019

(54) RASPBERRY PLANT VARIETY NAMED 'DRISRASPELEVEN'

(50) Latin Name: ***Rubus idaeus* L.**
Varietal Denomination: DrisRaspEleven

(71) Applicant: Driscoll's, Inc., Watsonville, CA (US)

(72) Inventors: Brian K. Hamilton, Richmond, TX (US); Thomas M. Sjulin, Aromas, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 15/932,178

(22) Filed: Feb. 15, 2018

(51) Int. Cl.
*A01H 5/08* (2018.01)

(52) U.S. Cl.
USPC ..... Plt./204
CPC ..... *A01H 5/08* (2013.01)

(58) Field of Classification Search
USPC ..... Plt./204
CPC ..... A01H 5/0887
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP7,528 | P | 5/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |
| PP27,644 | P3 | 2/2017 | Hamilton et al. |
| PP28,775 | P2 | 12/2017 | Hamilton et al. |
| PP28,856 | P3 | 1/2018 | Vitten et al. |

OTHER PUBLICATIONS

Cousineau et al., "Use of Isoenzyme Analysis to Characterize Raspberry Cultivars and Detect Cultivar Mislabeling", HortScience vol. 27, No. 9, Sep. 1992, pp. 1023-1025.
Williams et al., "DNA Polymorphisms Amplified by Arbitrary Primers are Useful as Genetic Markers", Nucleic Acids Research, vol. 18, No. 22, 1990, pp. 6531-6535.
Unpublished U.S. Appl. No. 15/732,501, filed Nov. 20, 2017, titled "Raspberry Plant Variety Named DrisRaspTwelve".
Unpublished U.S. Appl. No. 15/731,419, filed Jun. 6, 2017, titled "Raspberry Plant Variety Named DrisRaspThirteen".

*Primary Examiner* — Kent L Bell
(74) *Attorney, Agent, or Firm* — Morrison & Foerster LLP

(57) ABSTRACT

A new and distinct variety of raspberry plant named 'DrisRaspEleven', particularly characterized by its large fruit, red fruit color, and its ability to withstand mechanical harvesting, is disclosed.

4 Drawing Sheets

Latin name:
Botanical classification: *Rubus idaeus* L.
Varietal denomination: The varietal denomination of the claimed variety of raspberry plant is 'DrisRaspEleven'.

BACKGROUND OF THE INVENTION

Raspberries are the edible fruit of a multitude of plant species in the genus *Rubus* of the rose family. Most raspberry species are in the subgenus Idaeobatus. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubus idaeus* L), which has been denominated as 'DrisRaspEleven'.

Raspberry plant variety 'DrisRaspEleven' was discovered in Whatcom County, Wash. in August of 2009 and originated from a cross between the proprietary female parent raspberry plant 'V:312.1' (unpatented) and the proprietary male parent raspberry plant 'RB721.1' (unpatented). The original seedling of the new variety was first asexually propagated via cuttings in 2009.

'DrisRaspEleven' was subsequently asexually propagated via root cuttings, and underwent further testing at a farm in Whatcom County, Wash. for seven years (2009 to 2015). The present invention has been found to be stable and reproduce true to type through successive asexual propagations via root cuttings.

'DrisRaspEleven' exhibits the following distinguishing characteristics when grown under normal horticultural practices in Whatcom County, Wash.:

1. Large fruit size;
2. Bright red color fruit;
3. Good flavor; and
4. Better shelf life.

'DrisRaspEleven' was selected for its large fruit, red fruit color, and its ability to withstand mechanical harvesting.

BRIEF DESCRIPTION OF THE DRAWINGS

This new raspberry plant is illustrated by the accompanying photographs, which show fruit of the plant, as well as a cane, flowers, and leaves. The colors shown are as true as can be reasonably obtained by conventional photographic procedures. The photographs are of plants that are two years old.

DETAILED BOTANICAL DESCRIPTION

Figures 1A, 1B:
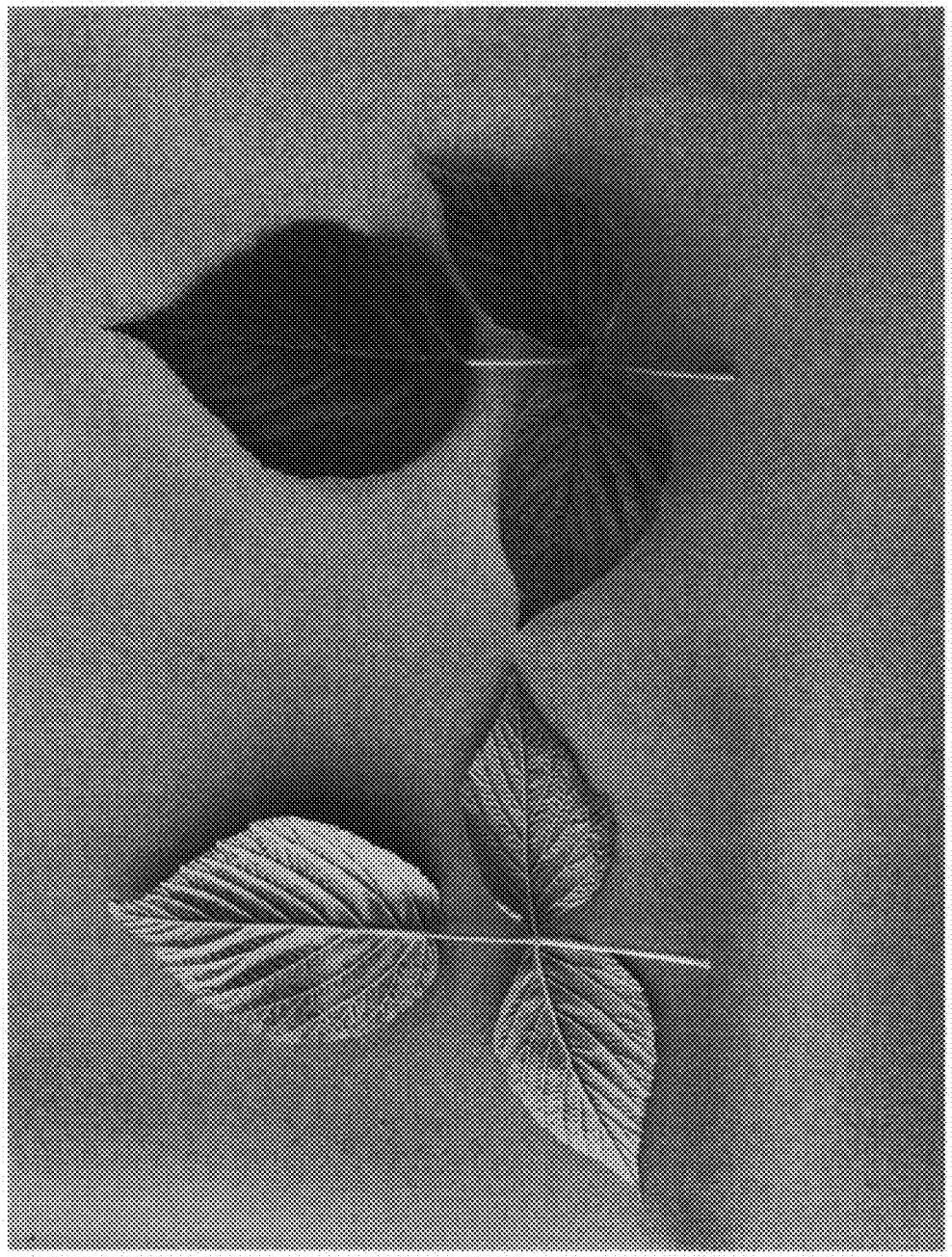
FIGS. 1A and 1B illustrate both the lower surface (FIG. 1A) and the upper surface (FIG. 1B) of plant leaves of variety 'DrisRaspEleven'.
Figure 2:
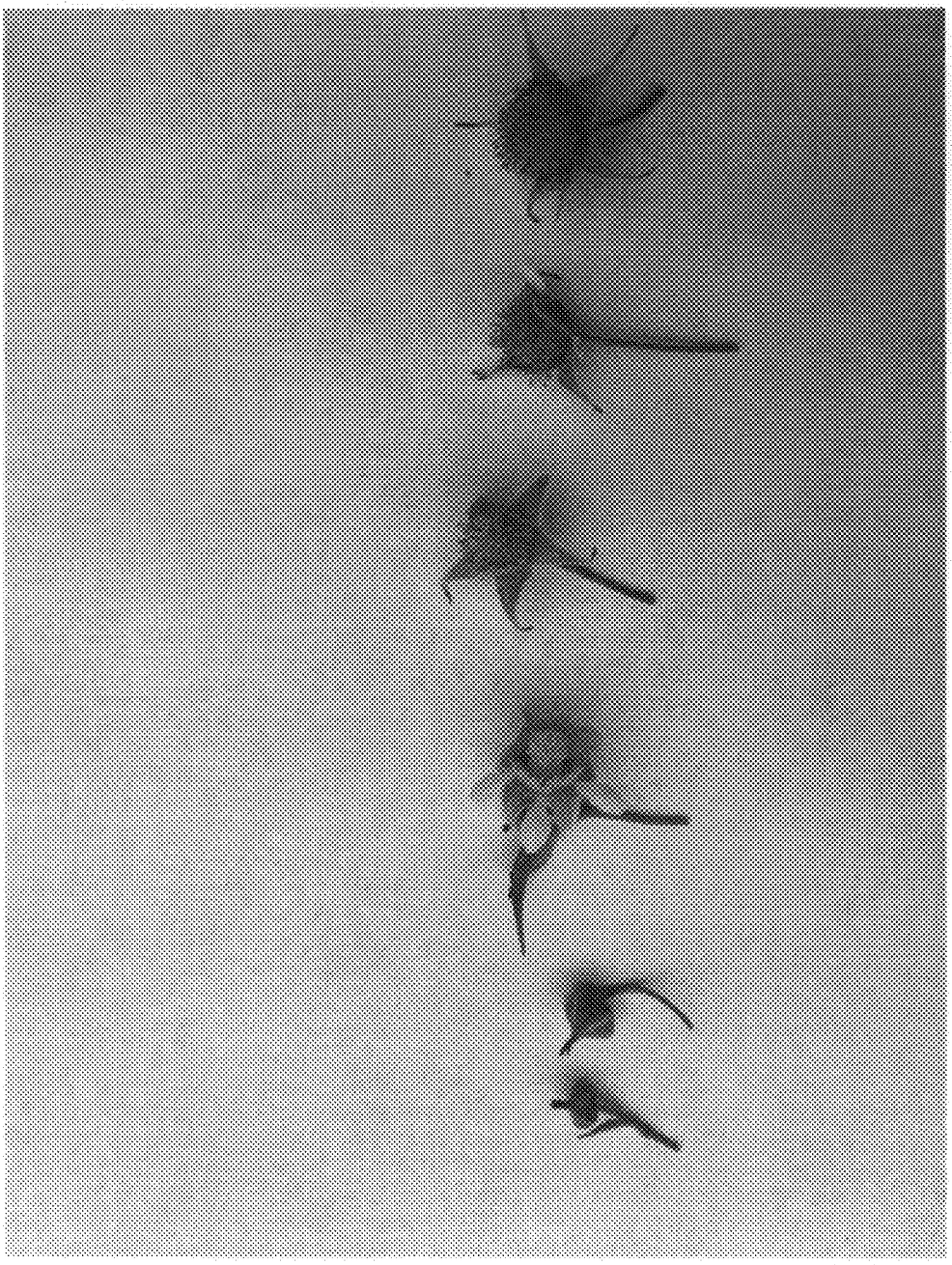
FIG. 2 illustrates typical flowers of variety 'DrisRaspEleven' at various stages of development.
Figure 3:
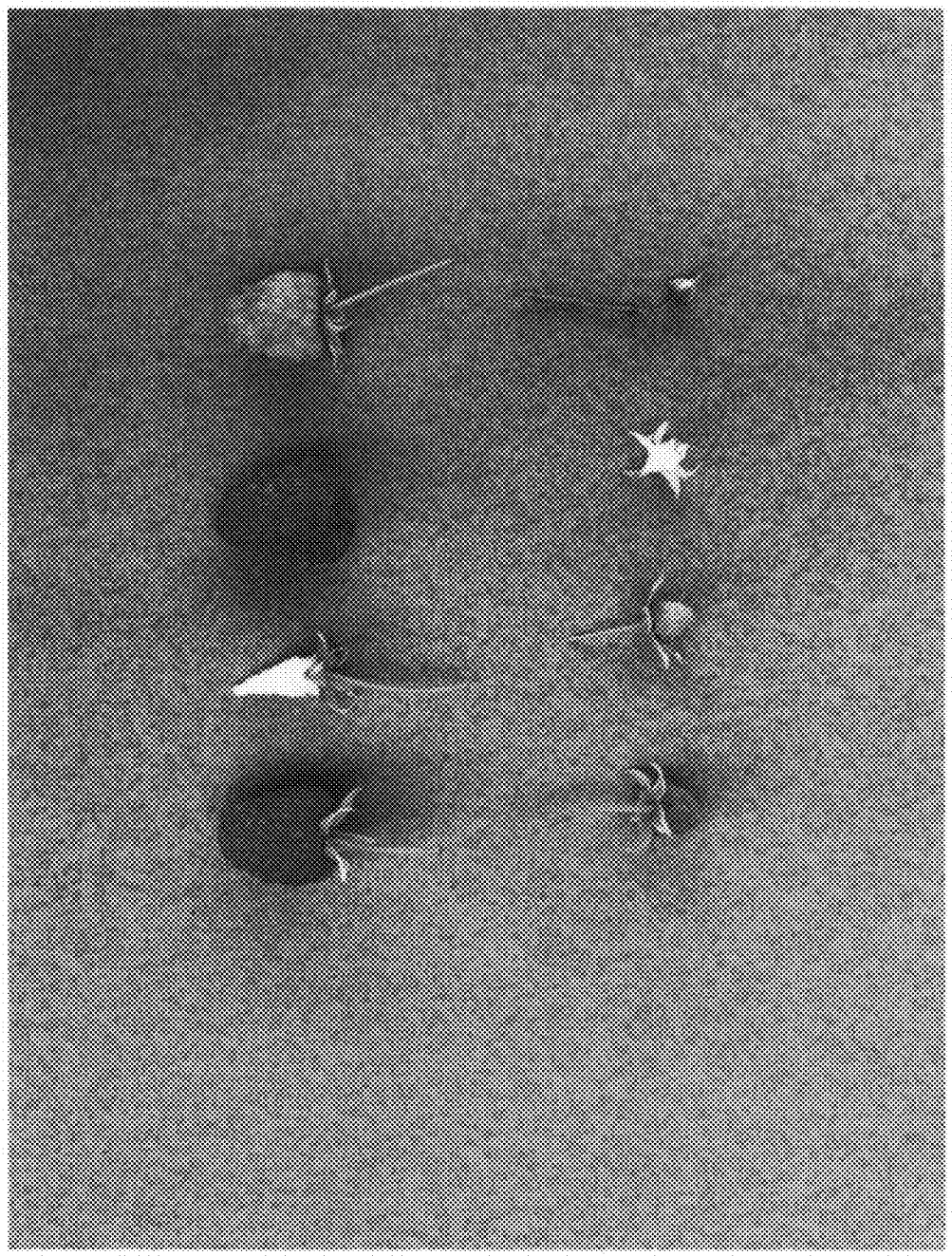
FIG. 3 illustrates typical fruit of variety 'DrisRaspEleven' at various stages of development.
Figure 4:
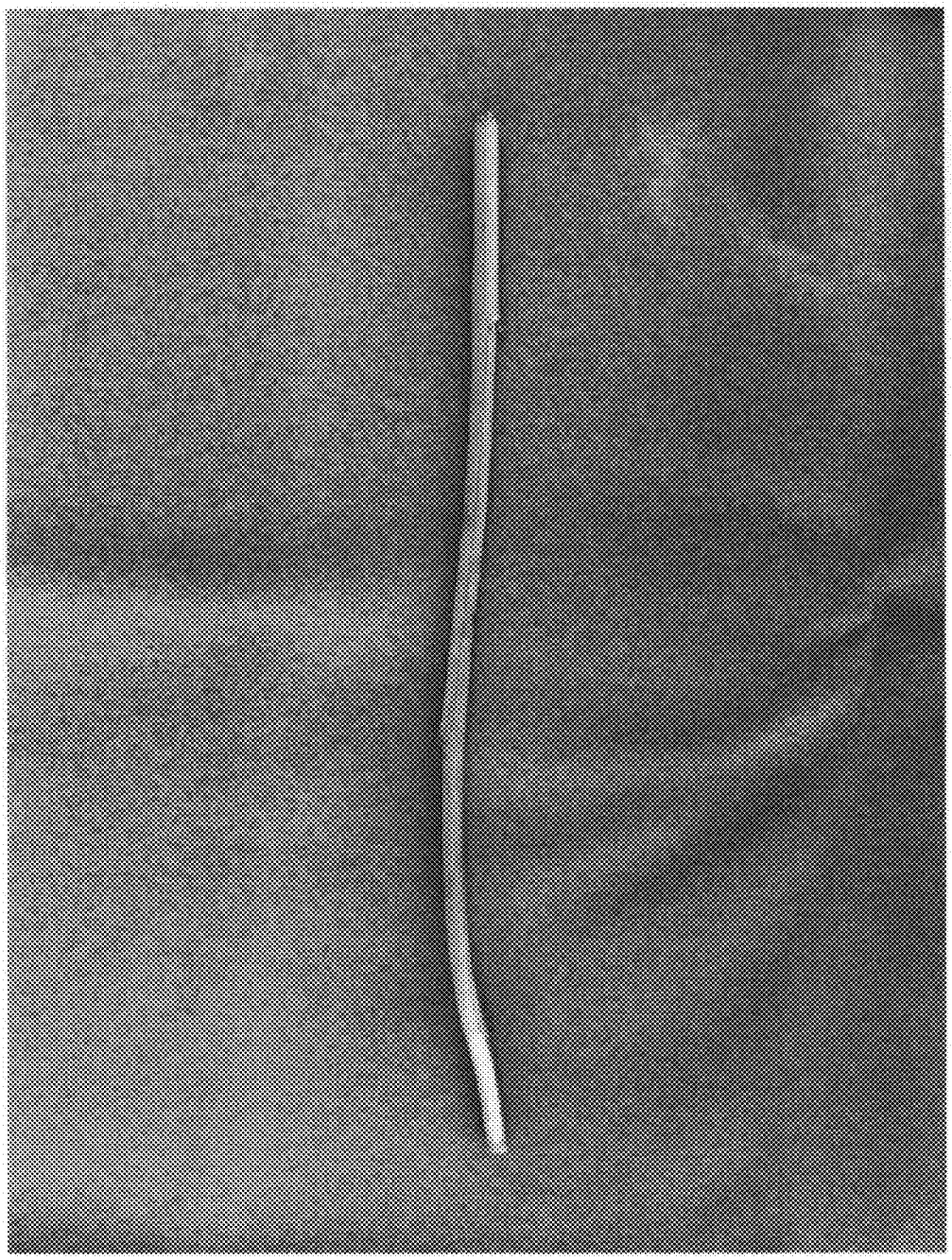
FIG. 4 illustrates a section of a cane of variety 'DrisRaspEleven'.

The following descriptions set forth the distinctive characteristics of 'DrisRaspEleven'. The data that define these characteristics are based on observations taken in Whatcom County, Wash. from 2009 to 2015. This description is in accordance with UPOV terminology. Color designations, color descriptions, and other phenotypical descriptions may deviate from the stated values and descriptions depending upon variation in environmental, seasonal, climatic and cultural conditions. 'DrisRaspEleven' has not been observed under all possible environmental conditions. The botanical description of 'DrisRaspEleven' was taken from two-year-old plants. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary, 2nd* edition by James G. Harris and Melinda Woolf Harris, unless where otherwise defined.

Classification:
- *Family*.—Rosaceae.
- *Botanical*.—*Rubus idaeus* L.
- *Common name*.—Raspberry.
- *Variety name*.—'DrisRaspEleven'.

Parentage:
- *Female parent*.—'V312.1' (unpatented).
- *Male parent*.—'RB721.1' (unpatented).

Plant:
- *Propagation*.—Root cuttings.
- *Height*.—216.50 cm.
- *Width*.—184.20 cm.
- *Length/width ratio*.—1.2.
- *Self-fruitfulness*.—Self-fruitful.
- *New cane growth habit*.—Semi-erect or semi-upright.

Primocanes:
- *Cane length in autumn*.—146.50 cm.
- *Internodal distance at central ⅓ of cane*.—5.65 cm.
- *Anthocyanin coloration of apex during rapid growth of very young shoot*.—Present.
- *Shape of cane cross section (from mid cane of primocane)*.—Rounded.
- *Pubescence on canes*.—Absent.

Floricanes:
- *Dormant cane color in summer*.—RHS 60B (Strong purplish red).
- *Fruiting lateral attitude in summer*.—Semi-erect.

Prickles (spines):
- *Length at* 1.0 *m height at end of harvest season (from base to tip)*.—1.50 mm.
- *Color (pigmentation)*.—RHS 138B (Moderate yellow-green).
- *Attitude of tip*.—Upward.
- *Presence and distribution on petioles*.—Absent.

Leaves:
- *Terminal leaflet*.—Length: 112.8 mm. Width: 74.9 mm. Length/width ratio: 1.5. Leaf color: Green color of upper surface: RHS 137A (Moderate olive-green). Green color of lower surface: RHS 138B (Moderate yellow-green). Profile in cross section: Concave. Overlapping or relative position of lateral leaflets:

Free (In some terminal leaflets one side of the basal pair leaflet is attached to terminal leaflet). Shape: Ovate. Apex: Truncate. Base: Obtuse. Margin: Doubly serrate.

*Lateral leaflets* (*basal pair*).—Number of leaflets: Usually 3. Size: Length: 93.8 mm. Width: 59.3 mm. Length/width ratio: 1.6. Shape: Ovate. Base: Obtuse. Margin: Doubly serrate.

*Rachis length between terminal leaflet and adjacent lateral leaflets*.—30.91 mm.

*Petiole*.—Length: 4.12 mm. Diameter: 1.72 mm. Pigmentation of upper surface: RHS 138A (Moderate yellowish green). Pigmentation of underside: RHS 138B (Moderate yellow-green).

Stipules:

*Orientation*.—Erect.

Flowers:

*Diameter*.—22.45 mm.

*Petal length*.—6.39 mm.

*Petal width*.—3.45 mm.

*Length/width ratio*.—1.9.

*Petal color*.—RHS 139D (Moderate yellow-green).

*Flowering period*.—Floricane: Early July to late August.

*Pedicel*.—Anthocyanin coloration: Present. Length: 23.77 mm. Diameter: 1.03 mm.

Fruit:

*Brix value*.—9.1.

*Length*.—24.51 mm.

*Diameter*.—23.40 mm.

*Ratio of length to width*.—1.0.

*Average number of drupelets per fruit*.—85.

*Weight* (*g/fruit*).—Floricane: 9.1 g/fruit.

*Weight of seeds*.—0.003295 g/seed.

*Shape*.—Ovate (Broad conical).

*Color*.—Maturing fruit: RHS 41A (Vivid reddish orange). Mature fruit color: RHS 46A (Strong red).

*Main bearing type*.—Only on previous year's cane in summer.

*Harvest season*.—Time of ripening — floricane: Early July to late August.

*Yield*.—20,000 kg/ha to 27,000 kg/ha of fruit per season from 25-month-old plants when grown in Whatcom County, Wash.

COMPARISONS TO PARENTAL AND COMMERCIAL RASPBERRY VARIETIES

'DrisRaspEleven' differs from the proprietary female parent 'V312.1' (unpatented) in that 'DrisRaspEleven' produces fruit that is larger, sweeter, and has a brighter red color than that produced by 'V312.1'. Additionally, 'DrisRaspEleven' produces plants that are higher yielding than 'V312.1' plants.

'DrisRaspEleven' differs from the proprietary male parent 'RB721.1' (unpatented) in that 'DrisRaspEleven' produces fruit with a sweeter flavor than that produced by 'RB721.1'. Additionally, 'DrisRaspEleven' produces plants that are higher yielding than 'RB721.1' plants.

When 'DrisRaspEleven' is compared to the commercial variety 'Willamette' (unpatented), 'DrisRaspEleven' produces fruit with a sweeter processing flavor than fruit produced by 'Willamette'.

When 'DrisRaspEleven' is compared to the commercial variety 'Meeker' (unpatented), 'DrisRaspEleven' produces fruit with a larger size than that of 'Meeker'.

What is claimed is:

1. A new and distinct variety of raspberry plant designated 'DrisRaspEleven' as shown and described herein.

* * * * *